United States Patent [19]

Thompson

[11] Patent Number: 5,684,051
[45] Date of Patent: Nov. 4, 1997

[54] MEDICAL DEVICES WITH IMPROVED ELASTIC RESPONSE

[75] Inventor: Samuel Anthony Thompson, Wilmington, Del.

[73] Assignee: Hercules Incorporated, Wilmington, Del.

[21] Appl. No.: 637,018

[22] Filed: Apr. 24, 1996

[51] Int. Cl.$^6$ ............... A61K 47/36; A61K 9/14; A61K 9/22; A61K 2/02
[52] U.S. Cl. ............. 514/777; 514/778; 514/779; 514/781; 514/782; 523/113; 523/115; 604/891.1
[58] Field of Search ................ 514/777, 778, 514/779, 781, 782; 523/113, 115; 604/891.1

[56] References Cited

U.S. PATENT DOCUMENTS

| | | | |
|---|---|---|---|
| 3,271,496 | 9/1966 | Michaels | 264/232 |
| 3,608,057 | 9/1971 | Bixler | 264/322 |
| 4,286,341 | 9/1981 | Greer et al. | 427/2 |
| 4,808,182 | 2/1989 | Barrett | 623/6 |
| 4,878,907 | 11/1989 | Okada et al. | 623/1 |
| 4,902,295 | 2/1990 | Walthall et al. | 623/11 |
| 4,941,870 | 7/1990 | Okada et al. | 600/36 |
| 4,997,443 | 3/1991 | Walthall et al. | 623/11 |
| 5,057,606 | 10/1991 | Garbe | 536/54 |
| 5,085,629 | 2/1992 | Goldberg et al. | 604/8 |
| 5,531,735 | 7/1996 | Thompson | 604/891.1 |

FOREIGN PATENT DOCUMENTS

| | | |
|---|---|---|
| 0507604 | 10/1992 | European Pat. Off. |
| 0645150 | 3/1995 | European Pat. Off. |

*Primary Examiner*—Carlos Azpuru
*Attorney, Agent, or Firm*—Martin F. Sloan

[57] ABSTRACT

Elastically deformable medical devices, such as stents, having improved speed and degree of shape recovery are made by treating shaped hydrogels containing a polymer with a solution containing at least one elasticity agent, which may be nonionic or ionic. For example, polysaccharide-based hydrogels, such as barium alginate, are formed into tubing, shaped into pigtail stents, and exposed to an aqueous solution containing an elasticity agent such as potassium ions, sodium ions, sorbitol, glucose, citric acid, mannitol, dulcitol, or glycerol. The solution may also contain a crosslinking agent, such as calcium ions, to achieve the desired degree of elasticity.

66 Claims, No Drawings

MEDICAL DEVICES WITH IMPROVED ELASTIC RESPONSE

FIELD OF THE INVENTION

This invention relates to hydrogel medical devices with improved elastic response and to methods for preparing such medical devices. More particularly, the invention pertains to medical devices made from polymeric hydrogels treated with an elasticity agent, which improves the speed and degree of shape recovery following deformation of the medical device, e.g., for insertion into the body.

BACKGROUND OF THE INVENTION

Medical devices are often used to facilitate the flow of material, as, for example, in a ureteral stent used for drainage of urine from the kidney to the bladder, or in a vascular graft used to maintain blood flow. Typically, these medical devices have been made from durable, non-biodegradable materials such as metals, polyurethanes, and polyacrylates. These non-biodegradable, non-dissolvable medical devices typically must be removed via an invasive procedure after they have served their purpose, otherwise they remain in the body indefinitely. For those devices which remain in vivo, there are often medical complications such as inflammation and other foreign-body responses.

Devices have also more recently been prepared from biodegradable materials such as polyesters, polyanhydrides, and polyorthoesters. In U.S. Pat. No. 5,085,629, the use of a biodegradable polyester terpolymer of lactide, glycolide, and epsilon-caprolactone in a ureteral stent is disclosed. In that patent, biodegradable has been defined to include hydrolyric instability. These polymers undergo hydrolytic chain cleavage in the presence of water to form low molecular weight water-soluble species. The polyesters have been reported to undergo hydrolysis throughout the thickness of the device (homogeneous hydrolysis), while the polyanhydrides and polyorthoesters have been reported to hydrolyze from the surface (heterogeneous hydrolysis). There are several problems inherent to medical devices manufactured with these biodegradable materials. There is a significant loss of strength in the device prior to any significant weight loss. These devices may undergo failure into large pieces, which may occlude the vessel in which they have been deployed, with potentially catastrophic consequences to the patient. Biodegradable devices that undergo surface hydrolysis may eventually reach a thin-skin configuration, which may also lead to vessel occlusion. Semicrystalline biodegradable materials have also been shown to leave insoluble crystalline residuals in the body for very long periods of time.

Polysaccharide-metal salt systems have been used for many years in biomedical applications. In European Patent Application No. 507 604 A2, an ionically crosslinked carboxyl-containing polysaccharide is used in adhesion prevention following surgery. The ionically crosslinked polysaccharide of this publication is left in vivo. No attempt to dissolve the material is made.

Hydrogels have been widely used in biomedical applications. U.S. Pat. Nos. 4,941,870, 4,286,341, and 4,878,907 disclose the use of a hydrogel as a coating on an elastomer base in a vascular prosthesis. This hydrogel remains in vivo. Kocavara et al. (*J. Biomed. Mater. Res.*, vol. 1, 1967, pp. 325–336) have reported using an anastomosis ureteral prosthesis prepared from a poly(hydroxyethyl methacrylate) hydrogel reinforced with polyester fibers. This prosthesis is designed to be left in vivo.

U.S. Pat. Nos. 4,997,443 and 4,902,295 disclose the preparation of transplantable artificial pancreatic tissue from an alginic acid gel precursor, a matrix monomer, and pancreas cells with $Ca^{2+}$ ions and a matrix monomer polymerization catalyst. The calcium-alginic acid is used to provide mechanical integrity to the mixture while the matrix monomer is polymerized, after which the calcium-alginic acid is removed with citrate via calcium chelation to leave a porous matrix. This use of the chelate to dissolve the calcium-alginic acid takes place in vitro. The calcium-alginic acid functions as a processing aid, not as a structural member, in the final artificial-tissue device.

Polysaccharide-metal salt hydrogels have also been used to prepare tiny gel capsules containing pancreatic islet cells for the production of insulin. These capsules have been shown by workers at the Veterans Administration Wadsworth Medical center to effectively control insulin levels in diabetic dogs for two years (Scientific American, June 1992, pp. 18–22). These capsules remain in vivo.

U.S. Pat. No. 5,057,606 discloses a method and article useful for preparing polysaccharide hydrogels. These foamed and non-foamed gelled articles are prepared by mixing together a first component comprising a suspension of a water insoluble di- or tri-valent metal salt in an aqueous solution of a polysaccharide, with a second component comprising an aqueous solution of a water-soluble acid optionally to include the water-soluble polysaccharide. These gels remain in vivo.

Commonly owned U.S. Ser. No. 08/128,952, filed Sep. 29, 1993, in the name of Luzio and Thompson, the disclosure of which is incorporated by reference herein, which corresponds to European Patent Publication No. 0 645 150 A1, describes hydrogel medical devices that eliminate the problems associated with the materials discussed above. Hydrolyric instability is not relied upon to facilitate dissolution. The devices are disintegrated upon demand through application of an agent that acts to remove ionic crosslinking species, which may be anionic (mono or poly) or cationic (mono or poly) in nature, via binding or displacement mechanisms. Triggered disintegration (breakdown of the device into small particulates and water-soluble components) eliminates the time uncertainty observed with bioerodible materials from one patient to the next. Methods for triggered disintegration include administering or triggering release of the disintegration agent through the diet, administering the agent directly onto the device in an aqueous solution, encapsulating the agent in the device, parenteral feeding, and enema. Disintegration occurs without significant swelling of the device.

U.S. Pat. Nos. 3,608,057 and 4,808,182 describe methods for making contact and intraocular lenses. These methods employ a plasticizer or hyperosmotic solution to treat a lens made from a polymeric or hydrogel composition, which causes substantial dehydration of the composition.

Hydrogels offer excellent biocompatibility and have been shown to have a reduced tendency for inducing thrombosis, encrustation, and inflammation. Unfortunately, as a result of their high water content, hydrogels typically suffer from poor strength and low stiffness.

Ionically crosslinked hydrogels, e.g., polysaccharide gels such as alginate gels, can be very elastic and rubbery in nature. Strong and stiff hydrogels can be prepared by increasing the crosslink density and polymer (e.g., polysaccharide) concentration in the gel. As crosslink density and polymer concentration are increased to improve strength, however, the elastic nature of the gel is sacrificed.

In addition to losing elasticity, the gels typically become more sluggish (i.e., their speed of elastic response becomes slower).

The sluggish response is especially noticeable around and below room temperature—the temperature to which a medical device is usually exposed when handled outside of the body. In a medical device requiring shape memory, for example, a double-pigtail ureteral stent, a strong alginate gel will exhibit very slow and often incomplete recovery of the pigtail. Therefore, the use of polysaccharide-based hydrogels in medical devices can be limited by strength and shape recovery characteristics.

Glycerol, sorbitol, 1,2-propane diol, 2-propanol, ascorbic acid, hexamethylene glycol, urea, and triethanolamine are well-known plasticizers for dry polysaccharide films and fibers. These dry film plasticizers act to toughen and increase elongation to failure in dry films and fibers. However, the art is in need of an effective way to increase the speed and degree of recovery in hydrogels without substantial dissolution, degradation, or dehydration of the hydrogel composition.

SUMMARY OF THE INVENTION

An object of this invention is to provide a means for improving the speed and degree of shape recovery in hydrogels, particularly polysaccharide hydrogels, used to form medical devices. A substantially rapid and complete elastic response after deformation allows for more aggressive handling by a physician during insertion. Where the device must be deformed prior to insertion into the body, the present invention facilitates essentially complete and rapid shape recovery of the device after insertion.

Another object of the invention is to achieve a method for conveniently preparing a hydrogel medical device having a desirable blend of properties, e.g., strength and elastic response to deformation.

These and other objects have been achieved by a medical device according to the invention, which comprises a shaped, elastically deformable portion (i.e., part or all of the device) prepared from a hydrogel composition comprising a polymer, the elastically deformable portion having been exposed after shaping to a solution comprising an elasticity agent in an amount sufficient to enhance elastic response without substantial dissolution, degradation, or dehydration of the hydrogel composition. Treatment of the hydrogel composition with the elasticity agent does not cause dehydration such that there is significant deswelling or reduction in size.

Preferably, the solution containing the elasticity agent is aqueous. A preferred concentration of the elasticity agent is greater than about 0.5 percent by weight of the solution, more preferably about 1–50 percent by weight of the solution.

The invention is also directed to a method of preparing such a medical device. Thus, the invention is directed to a method of making a medical device having an improved elastic response, comprising preparing an elastically deformable hydrogel composition comprising a polymer; shaping the hydrogel composition; and exposing the shaped hydrogel composition to a solution comprising an elasticity agent in an amount sufficient to enhance elastic response without substantial dissolution, degradation, or dehydration of the hydrogel composition.

The hydrogel composition preferably comprises an ionically or covalently crosslinked polymer, more preferably an ionically crosslinked polysaccharide, such as an alginate gel.

According to one embodiment of the invention, the elastic response of an ionically crosslinked polymeric hydrogel, such as a medical device made from a strong alginate gel, is improved by adding one or more elasticity agents, which may be ionic or nonionic, to the environment, which is preferably aqueous, surrounding the gel.

An exemplary ionic elasticity agent contains one or more ions selected from sodium, potassium, magnesium, silver, ammonium, and lithium. Preferred ionic elasticity agents include monovalent cations, such as sodium or potassium, or divalent non-crosslinking cations, such as magnesium. These agents act by displacing the crosslinking metal ions (e.g., barium, calcium, copper, cobalt, aluminum, iron, boron, beryllium, lead, or silver) from the alginate gel. The elastic response of strong gels is improved upon exposure to these monovalent and divalent ions in the environment surrounding the gel.

Certain nonionic agents, e.g., those containing hydroxyl or amine groups, may also be used for increasing the elastic response of gels. As with the ionic agents of the invention, slight swelling of the gel may occur in the presence of the nonionic agents. Exemplary nonionic agents contain at least one hydroxyl or amine group, and include low molecular weight sugars and sugar metabolites (e.g., sorbitol), citric acid, and glycerol. Preferred nonionic agents are glucose, sorbitol, citric acid, urea, and glycerol.

The environment, which is preferably an aqueous solution, may further contain crosslinking ions of one or more types, such as barium, calcium, strontium, and copper ions, to achieve the desired degree of gel elasticity.

A preferred polymer is a polysaccharide, which may be selected from alginic acid, pectinic acid, hyaluronic acid, cellulose, chitosan, chitin, starch, dextran, heparin, chondroitin, cationic guar, cationic starch, carboxymethyl cellulose, carboxymethyl chitosan, carboxymethyl dextran, carboxymethyl starch, heparin sulfate, and chondroitin sulfate. In a preferred embodiment, the polymer is ionically crosslinked. For example, the polymer can be cationically crosslinked with an ionic crosslinking agent selected from barium, calcium, magnesium, strontium, boron, beryllium, aluminum, iron, copper, cobalt, lead, and silver ions. Preferred ionic crosslinking agents are barium, calcium, strontium, and copper ions, more preferably barium ions.

In a preferred embodiment, the hydrogel polymer is a polysaccharide and the elasticity agent is ionic. In another embodiment, the polymer is a polysaccharide and the elasticity agent is nonionic, e.g., sorbitol, urea, or citric acid. In these embodiments, the polysaccharide is preferably alginic acid, pectinic acid, hyaluronic acid, cellulose, chitosan, chitin, starch, dextran, heparin, chondroitin, cationic guar, cationic starch, or a derivative or salt thereof. In an especially preferred embodiment, the gel composition is alginic acid or a salt thereof crosslinked with barium or calcium ions, and the gel is treated with an aqueous solution of the elasticity agent, which is selected from potassium ions, sodium ions, sorbitol, glucose, citric acid, mannitol, dulcitol, and glycerol.

The hydrogel composition optionally comprises further ingredients, such as a disintegrating agent. Exemplary disintegrating agents are inorganic sulfates, ethylene diamine tetraacetic acid, ethylene diamine tetraacetate, citrates, organic phosphates, inorganic phosphates, phosphoric acid, trisodium carboxymethyloxy succinate, nitrilotriacetic acid, maleic acid, oxalate, polyacrylic acid, and sodium, potassium, calcium, and magnesium ions. Preferred disintegrating agents are selected from inorganic sulfates, inorganic phosphates, and magnesium ions.

Exemplary medical devices according to the invention are stents, catheters, cannulas, plugs, and restrictors. In one preferred embodiment, the medical device is an elastically deformable stent having a retention feature, the entire stent having been exposed after shaping to the solution comprising the elasticity agent.

An especially preferred embodiment of a medical device of the invention is a ureteral stent having pigtail- or coil-retention features. Uretheral stents must be deformed by straightening out, e.g., over a guide wire or inside a scope, for insertion into the body. Shape recovery of the pigtails is key to the retention of the stent in the kidney and bladder.

Another preferred embodiment of a medical device according to the invention is a biliary stent. A biliary stent also requires deformable retention features, such as flaps, that must be pressed flat during the insertion procedure, after which they recover and provide physical retention against the wall of the bile duct.

DETAILED DESCRIPTION OF PREFERRED EMBODIMENTS

The invention overcomes performance drawbacks of the prior art by providing hydrogel medical devices, such as stents, with improved elastic-response properties. The improvement in the elastic response of the hydrogel, e.g., a strong polysaccharide gel, may be accomplished by treating the gel with at least one elasticity agent, for example, by adding an elasticity agent to an aqueous environment surrounding the gel. Elasticity agents that may be used in the invention can be classified as ionic or nonionic in nature.

Preferred ionic elasticity agents of this invention include monovalent cations, such as sodium, lithium, silver, ammonium, and potassium. Other preferred ionic agents are divalent non-crosslinking cations, for example magnesium for alginate gels. Such agents act by displacing crosslinking metal ions (e.g., barium, calcium, copper, cobalt, aluminum, iron, boron, beryllium, lead, or silver) from the hydrogel. Polysaccharide hydrogels typically have components that are capable of ionic or strong hydrogel bonding along the polymer chains, and the agents may act to shield inter- and intra-chain hydrogel bonding. The overall effect of such ionic agents is to increase the speed and degree of shape recovery of the gel.

Surprisingly, nonionic agents containing hydroxyl or amine groups also have been found to increase the speed and degree of shape recovery of hydrogels. The term "nonionic agent" means agents that are nonionic at about neutral pH. As with the ionic agents discussed above, slight swelling of the gel may occur in the presence of the nonionic agents.

Preferred nonionic agents include: low molecular weight sugars such as glucose; sugar metabolites such as sorbitol, mannitol, iditol, and dulcitol; citric acid; urea; and glycerol. Even more preferred nonionic agents are sorbitol, urea, and citric acid. An especially preferred agent for improving the elastic response of strong calcium and barium alginate gels is sorbitol—a natural metabolite of glucose. Both calcium and barium alginate ureteral stents stored in a solution of 50% sorbitol/50% water exhibit excellent elastic response and 100% complete pigtail recovery.

The elastic response of gels, and in particular strong gels, can be improved upon exposure of the gel to an environment comprising at least one elasticity agent. Optionally, the environment may further comprise at least one additional elasticity agent or one or more other ingredients, e.g., a crosslinking agent, to produce the desired degree of gel elasticity.

The environment is preferably an aqueous solution, with the elasticity agent being present in the solution in an mount sufficient to enhance elastic recovery of the shape without dissolving degrading, or dehydrating the hydrogel. Preferably, the shaped hydrogel is exposed to an aqueous solution containing no less than about 0.1 percent by weight of one or more elasticity agents, more preferably, no less than 0.5 percent, and even more preferably, no less than 1 percent. The shaped hydrogel is preferably exposed to no greater than 70 percent by weight of one or more elasticity agents, more preferably, no greater than 60 percent, and even more preferably, no greater than 50 percent. A preferred range for the concentration of the elasticity-agent solution is from about 1 weight percent to about 50 weight percent.

The hydrogel medical devices, or at least the elastically deformable portions thereof, are preferably stored in an aqueous environment containing the elasticity agent. If storage of the hydrogel in an ionic solution is not desired, hydrogels containing bound ionic groups may be prepared via exposure to the appropriate ionic elasticity agent, and then rinsed and stored in deionized water without loss of performance.

The term "hydrogel" or "gel" indicates a water-insoluble, water-containing material. The hydrogel composition comprises at least one polymer, which in one embodiment is a polysaccharide. In a preferred embodiment, the hydrogel composition comprises an ionically crosslinkable polymer, preferably a polysaccharide, and an ionic crosslinking agent. The hydrogel composition may optionally contain one or more other ingredients, e.g., fillers, medicaments, and disintegration agents.

The ionically crosslinkable polymers may be anionic or cationic in nature. Exemplary polymers include carboxylic-, sulfate-, and amine-functionalized polymers. Among the anionic polymers that may be employed are polyacrylic acid, polymethacrylic acid, alginic acid, pectinic acid, carboxymethyl cellulose, hyaluronic acid, heparin, carboxymethyl starch, carboxymethyl dextran, heparin sulfate, and chondroitin sulfate. Among the cationic polymers that may be used are chitosan, cationic guar, cationic starch, and polyethylene amine.

The polymer of the hydrogel is preferably a polysaccharide. Exemplary polysaccharide-based polymers include alginic acid, pectinic acid, hyaluronic acid, cellulose, chitosan, chitin, starch, dextran, heparin, chondroitin, cationic guar, cationic starch, and derivatives and salts thereof, such as carboxymethyl cellulose, carboxymethyl chitosan, carboxymethyl dextran, carboxymethyl starch, heparin sulfate, and chondroitin sulfate. Especially preferred polysaccharides are alginic acid, pectinic acid, and hyaluronic acid, and their salts.

The ionic crosslinking agents are generally categorized as anionic or cationic. Suitable cationic crosslinkers include barium, calcium, magnesium, strontium, boron, beryllium, aluminum, iron, copper, cobalt, lead, and silver. Barium, calcium, strontium, and copper are preferred cations, with barium being most preferred. Anionic crosslinkers are generally derived from polybasic organic or inorganic acids. Appropriate anionic crosslinkers include phosphate, citrate, borate, succinate, maleate, adipate, and oxalate ions, with phosphate ions being preferred.

Optionally, the hydrogel may include or be exposed to a disintegration agent, which functions upon being triggered by displacing a crosslinking ion. Suitable disintegration agents include inorganic sulfates, ethylene diamine tetraacetic acid and ethylene diamine tetraacetate, citrates, organic phosphates (e.g., cellulose phosphate), inorganic phosphates (e.g., pentasodium tripolyphosphate, mono- and di-basic potassium phosphate, sodium pyrophosphate), phosphoric acid, trisodium carboxymethyloxy succinate, nitrilotriacetic acid, maleic acid, oxalate, polyacrylic acid, and sodium, potassium, calcium, and magnesium ions. Inorganic sulfates, inorganic phosphates, and magnesium ions are preferred disintegration agents.

Examples of other optional ingredients or components of the hydrogel composition include treating agents or medicinal additives such as antiseptics, antibiotics, anticoagulants, pharmaceutical compounds, and the like.

The hydrogel composition is formed into an appropriate form for the desired medical device. The forming may be achieved by an appropriate technique, e.g., by extruding or molding the hydrogel. Additional or secondary shaping is used as appropriate, e.g., to form retention features. For example, stents having pigtail-shaped retention features may be formed by extruding a hydrogel composition into the form of tubing, cutting the tubing into appropriate lengths, shaping the cut tubing to form retention features, and treating the shaped stents with the elasticity agent (e.g., by immersion in a solution containing an elasticity agent). In a preferred embodiment of preparing such pigtail stents, the hydrogel composition comprises an ionically crosslinked polymer and the retention features are formed by steps comprising: (i) winding the ends of the hydrogel tubing lengths under tension around the pins of a shaping jig; (ii) immersing the wound tubing in an electrolyte solution, e.g., one containing water and potassium chloride, to strip the crosslinks; and (iii) re-crosslinking the hydrogel, e.g., by immersing the crosslink-stripped hydrogel in a crosslinking agent.

Systems in which the medical devices of the invention are useful include cardiovascular, lymphatic, neurological, integumental, skeletal, muscular, optical, otorhinolaryngological, oral, gastrointestinal, and urogenital systems. Medical devices that may be made in accordance with the invention include ureteral, urethral, bilial, ileal, and pyloric stents. Other exemplary medical devices include drainage devices (e.g., ear and sinus tubes), delivery devices, temporary plugs, and enteral feeding tubes and plugs. As evident from the following illustrative examples, elastically deformable pigtail stents may be advantageously prepared according to the invention.

EXAMPLES

Polysaccharide-based hydrogels in the form of hollow tubes each having a pigtail on at least one end were prepared as described in Examples A and B. Exemplary hydrogel medical devices in accordance with the invention were then prepared and tested for their elastic response, as described in Examples 1–8. In general, the procedure entailed the following steps:

(a) treating the polysaccharide-based hydrogel in an aqueous solution of an elasticity agent;

(b) deforming the treated hydrogel such that the pigtail is straightened; and (c) releasing the pigtail such that the hydrogel is allowed to return to the pigtail shape, and qualitatively observing the degree of recovery and speed of recovery of the pigtail.

EXAMPLE A—Preparation of Calcium Aiginate Pigtails

Part 1

Sodium alginate (121.2 g of Pronova Protanal LF 10/60) was weighed into a 4"×5" (10 cm×13 cm) aluminum pan. Deionized water (625.8 g) was weighed into a 1000-ml beaker. The beaker with water was placed under an overhead mixer, and the mixing blade was lowered off-center into the water. The mixer was operated at its highest speed to stir the water while the sodium alginate (Pronova Protanal LF 10/60) was quickly poured into the beaker.

After the sample was stirred for about 10 seconds, it was covered with Saran wrap and stored at room temperature in a hood overnight. The sample (718.2 g) was added to a Ross double planetary mixer, and the solution was mixed in the mixer at 60° C. for 30 minutes. Then 54.1 g of bismuth subcarbonate were added, followed by mixing for an additional 30 minutes. The mixture was allowed to cool in the Ross mixer.

The mixture was loaded into sterile 30-cc syringes, and the syringes were centrifuged to remove entrappeal air. The syringes were attached to a tubing die powered with a syringe pump, and tubing was extruded into a 30% calcium chloride dihydrate solution. The calcium chloride solution was also pumped through the center of the die as the tube was extruded. The tubing was left in the calcium solution overnight. The following day, the tubing was dialyzed in deionized water to remove excess ions.

Part 2

The tubing was cut into cylindrical lengths using a razor blade, and the cylindrical lengths were loaded onto pigtail-shaping jigs (plates each having two pins, around which the ends of the cylindrical lengths were coiled or wound to form pigtail-shaped ends). The loaded jigs were put into a stirred 25% potassium chloride solution for 40 minutes.

After 40 minutes, the jigs were pulled out of the potassium chloride bath and were transferred to a 30% calcium chloride dihydrate bath. The solution was stirred continuously for 60 minutes. The jigs were then removed from the solution and placed into a pan of deionized water. After about 30 minutes, the deionized water was poured out and was replaced with fresh deionized water. The fully shaped double-pigtail ureteral stents were cut from the jigs using a razor blade and were stored in deionized water.

EXAMPLE B—Preparation of Barium Alginate Pigtails

Lengths of calcium alginate tubing prepared as in Part 1 of Example A were loaded onto shaping jigs and were soaked for 40 minutes in a 25% KCl bath. Then the jigs were soaked for 1 hour in a 2.5% $BaCl_2 \cdot H_2O$ bath with constant mixing. The jigs were placed into deionized water. After 30 minutes, the water was poured out and replaced with fresh deionized water. After another thirty minutes, the water was changed again. Thirty minutes later, the water was replaced with 3000 g of an aqueous 0.15% sodium sulfate solution. After 10 minutes in the $Na_2SO_4$ solution, the solution was poured out and was replaced with fresh deionized water. This water was replaced after 30 total minutes had elapsed and again after 60 total minutes had elapsed. The fully shaped barium alginate pigtails were stored in deionized water.

EXAMPLE 1—Treatment with Potassium Salt

Barium alginate pigtails prepared as in Example B were placed into each of three jars containing potassium chloride in deionized water, with the first jar containing 0.5% KCl, the second jar containing 1.0% KCl, and the third jar containing 1.5% KCl. After soaking overnight at 37° C., the pigtails were straightened and the recovery response observed. The 0.5% KCl solution did not appreciably alter the pigtail recovery, while the 1.0% KCl and 1.5% KCl solutions significantly enhanced the speed and degree of recovery of the pigtails.

EXAMPLE 2—Treatment with Sodium and Calcium Salts

Calcium alginate pigtails prepared as in Example A were immersed in solutions containing a blend of NaCl (elasticity agent) and $CaCl_2.2H_2O$ (crosslinking agent). The compositions of the solutions and the results of pigtail recovery testing are listed in Table 1. Unless indicated otherwise, percentages and proportions given herein are by weight.

TABLE 1

| SOLUTION | RESPONSE |
| --- | --- |
| 0.5% NaCl + 0.07% $CaCl_2.H_2O$ (18/1 Na/Ca) | rapid recovery (much faster than control) |
| 0.5% NaCl + 0.127% $CaCl_2.H_2O$ (10/1 Na/Ca) | faster than control |
| 0.5% NaCl + 1.267% $CaCl_2.H_2O$ (1/1 Na/Ca) | faster than control |
| control (deionized water) | sluggish |

EXAMPLE 3—Treatment with Sorbitol

Calcium alginate and barium alginate pigtails prepared as in Examples A and B, respectively, were immersed in solutions of sorbitol in deionized water at concentrations of 5%, 10%, 20%, 40%, and 50%. The speed of recovery of both the barium alginate and calcium alginate pigtails improved as the level of sorbitol in the solution increased.

EXAMPLE 4A—Treatment with Glucose

Two solutions were prepared by dissolving 25 g of glucose in 25 g of deionized water in each of two jars. One calcium alginate pigtail prepared as in Example A was placed in one jar, and one barium alginate pigtail prepared as in Example B was placed in the other jar. The samples were warmed to 37° C. After 24 hours at 37° C., the samples were removed and pigtail response tested. Both the calcium alginate and the barium alginate pigtails exhibited significantly enhanced speed and degree of recovery from deformation over that observed with control samples, which had been soaked in deionized water.

EXAMPLE 4B—Treatment with Glucose

Two solutions were prepared by dissolving 15 g of glucose in 35 of deionized water in each of two jars. One calcium alginate pigtail prepared as in Example A was placed in one jar, and one barium alginate pigtail prepared as in Example B was placed in the other jar. The samples were warmed to 37° C. After 24 hours at this temperature, the samples were removed and tested for elastic response for recovery to the pigtail form. Both the calcium alginate and the barium alginate pigtails exhibited significantly enhanced speed and degree of recovery from deformation over that observed with control samples, which had been soaked in deionized water.

EXAMPLE 5—Treatment with Citric Acid

One barium alginate pigtail and one calcium alginate pigtail prepared according to Examples A and B, respectively, were each immersed in 2% citric acid monohydrate in deionized water. The samples were warmed to 37° C. and examined after 24 hours. Both the barium alginate and calcium alginate pigtails exhibited enhanced speed and degree of pigtail recovery over the control pigtails, which had been soaked in deionized water. The citric acid treatment also had the added effect of altering the surface feel of the gels in that the surface felt more rubbery and less slippery than the control pigtails.

EXAMPLE 6—Treatment with Mannitol

Twenty grams of mannitol were dissolved in 80 grams of deionized water at 90° C. A pigtail of calcium alginate and a pigtail of barium alginate prepared as in Examples A and B, respectively, were each immersed in the mannitol solution at 90° C., where the temperature was held for 45 minutes, and the samples were allowed to cool to room temperature. The pigtails were straightened and released. The barium alginate pigtail recovered 100% and was significantly faster to recover than the control barium alginate pigtail, which had been soaked in deionized water.

EXAMPLE 7—Treatment with Dulcitol

Ten grams of dulcitol were dissolved in 80 grams of deionized water at 90° C. A pigtail of calcium alginate and a pigtail of barium alginate prepared as in Examples A and B, respectively, were immersed in the mixture at 90° C., where the temperature was held for 45 minutes, and the samples were allowed to cool to room temperature. The pigtails were straightened and released. The barium alginate and calcium alginate pigtails recovered 100% and were significantly faster to recover than a control barium alginate and calcium alginate pigtails, which had been immersed in deionized water.

EXAMPLE 8—Treatment with Glycerol

One barium alginate pigtail prepared as described in Example B and one calcium alginate pigtail prepared as described in Example A were separately immersed in an aqueous (deionized water) 50% glycerol solution. The samples were warmed to 37° C., cooled, and then examined after 24 hours. Both the barium alginate and calcium alginate pigtails exhibited enhanced speed and degree of pigtail recovery over control pigtails, which had been soaked in deionized water.

COMPARATIVE EXAMPLES—Treatment with Dry Film Plasticizers

Calcium alginate pigtails prepared as described in Example A and barium alginate pigtails prepared as described in Example B were soaked in approximately 50 grams of the following solutions at 37° C. for three days. The pigtails were then evaluated for speed and degree of recovery after straightening of the pigtails. The results are summarized in the table below.

TABLE 2

| SOLUTION | PIGTAIL COMPOSITION | RESPONSE |
| --- | --- | --- |
| 2% ethanol amine | Ba alginate | sluggish, imcomplete recovery |
| | Ca alginate | sluggish, incomplete recovery |
| 5% ethanol amine | Ba alginate | sluggish, incomplete recovery |
| | Ca alginate | sluggish, incomplete reovery |
| 50% propylene glycol | Ba alginate | very slow, but complete recovery |
| | Ca alginate | very slow, but complete recovery |
| ascorbic acid | Ba alginate | sluggish, incomplete recovery |
| | Ca alginate | sluggish, incomplete recovery |

In comparison with the Comparative Examples, Examples 1–8 of the invention had significantly better speed and degree of recovery from deformation.

Other embodiments of the invention will be apparent to those skilled in the art through consideration of the specification and practice of the invention disclosed herein. It is intended that the specification and examples be considered as exemplary only, with the true scope and spirit of the invention being indicated by the following claims.

What is claimed is:

1. A medical device comprising a shaped, elastically deformable portion prepared from a hydrogel composition comprising a polymer, said elastically deformable portion having been exposed after shaping to a solution comprising an elasticity agent in an amount sufficient to enhance elastic response without substantial dissolution, degradation, or dehydration of the hydrogel composition.

2. A medical device according to claim 1, wherein the medical device is an elastically deformable stent having a retention feature, the entire stent having been exposed after shaping to the solution.

3. A medical device according to claim 1, wherein said polymer is a polysaccharide.

4. A medical device according to claim 3, wherein said polysaccharide is selected from the group consisting of alginic acid, pectinic acid, hyaluronic acid, cellulose, chitosan, chitin, starch, dextran, heparin, chondroitin, cationic guar, cationic starch, carboxymethyl cellulose, carboxymethyl chitosan, carboxymethyl dextran, carboxymethyl starch, heparin sulfate, and chondroitin sulfate.

5. A medical device according to claim 3, wherein said polysaccharide is selected from the group consisting of alginic acid, pectinic acid, and hyaluronic acid, and their salts.

6. A medical device according to claim 1, wherein said polymer has been ionically crosslinked.

7. A medical device according to claim 6, wherein said solution further comprises a crosslinking agent selected from the group consisting of barium, calcium, strontium, and copper ions.

8. A medical device according to claim 6, wherein said polymer has been cationically crosslinked with an ionic crosslinking agent selected from the group consisting of barium, calcium, magnesium, strontium, boron, beryllium, aluminum, iron, copper, cobalt, lead, and silver ions.

9. A medical device according to claim 8, wherein said crosslinking agent is selected from the group consisting of barium, calcium, strontium, and copper ions.

10. A medical device according to claim 6, wherein said polymer has been cationically crosslinked with a crosslinking agent containing barium ions.

11. A medical device according to claim 6, wherein said elasticity agent contains one or more ions selected from the group consisting of sodium, potassium, magnesium, silver, ammonium, and lithium ions.

12. A medical device according to claim 6, wherein said solution is aqueous.

13. A medical device according to claim 12, wherein said amount of the elasticity agent is greater than about 0.5 percent by weight of the solution.

14. A medical device according to claim 12, wherein said amount of the elasticity agent is about 1–50 percent by weight of the solution.

15. A medical device according to claim 1, wherein said elasticity agent is nonionic and contains at least one hydroxyl or amine group.

16. A medical device according to claim 1, wherein said elasticity agent is selected from the group consisting of glucose, sorbitol, citric acid, urea, and glycerol.

17. A medical device according to claim 1, wherein said elasticity agent is sorbitol.

18. A medical device according to claim 1, wherein said polymer is a polysaccharide and said elasticity agent is ionic.

19. A medical device according to claim 18, wherein said solution is aqueous.

20. A medical device according to claim 19, wherein said polysaccharide is alginic acid, pectinic acid, hyaluronic acid, cellulose, chitosan, chitin, starch, dextran, heparin, chondroitin, cationic guar, cationic starch, or a derivative or salt thereof.

21. A medical device according to claim 20, wherein said elasticity agent is selected from the group consisting of sodium, potassium, magnesium, silver, ammonium, and lithium ions, and mixtures thereof.

22. A medical device according to claim 1, wherein said polymer is a polysaccharide and the elasticity agent is nonionic.

23. A medical device according to claim 22, wherein said solution is aqueous.

24. A medical device according to claim 23, wherein said polysaccharide is alginic acid, pectinic acid, hyaluronic acid, cellulose, chitin, chitosan, starch, dextran, heparin, chondroitin, cationic guar, cationic starch, or a derivative or salt thereof.

25. A medical device according to claim 24, wherein said elasticity agent is selected from the group consisting of sorbitol, urea, and citric acid.

26. A medical device according to claim 1, wherein said polymer is alginic acid or a salt thereof crosslinked with barium or calcium ions, said solution is aqueous, and said elasticity agent is selected from the group consisting of potassium ions, sodium ions, sorbitol, glucose, citric acid, mannitol, dulcitol, and glycerol.

27. A medical device according to claim 26, wherein said elasticity agent is present in the solution in amount of from about 1 percent by weight to about 50 percent by weight.

28. A medical device according to claim 26, wherein the hydrogel composition further comprises a disintegrating agent selected from the group consisting of inorganic sulfates, inorganic phosphates, and magnesium ions.

29. A medical device according to claim 26, wherein the medical device is an elastically deformable stent having a retention feature, the entire stent having been exposed after shaping to the solution.

30. A medical device according to claim 1, wherein the hydrogel composition further comprises a disintegrating agent.

31. A medical device according to claim 30, wherein said disintegrating agent is selected from the group consisting of inorganic sulfates, ethylene diamine tetraacetic acid, ethylene diamine tetraacetate, citrates, organic phosphates, inorganic phosphates, phosphoric acid, trisodium carboxymethyloxy succinate, nitrilotriacetic acid, maleic acid, oxalate, polyacrylic acid, and sodium, potassium, calcium, and magnesium ions.

32. A medical device according to claim 1, wherein said polymer is a polysaccharide and the hydrogel composition further comprises an inorganic sulfate, inorganic phosphate, or magnesium ions.

33. A medical device according to claim 1, which is a stent, catheter, cannula, plug, or restrictor.

34. A method of making a medical device having an improved elastic response, comprising: preparing an elastically deformable hydrogel composition comprising a polymer; shaping the hydrogel composition; and exposing the shaped hydrogel composition to a solution comprising an elasticity agent in an amount sufficient to enhance elastic response without substantial dissolution, degradation, or dehydration of the hydrogel composition.

35. A method according to claim 34, wherein said shaping comprises forming the hydrogel composition into a stent having a retention feature.

36. A method according to claim 34, wherein said polymer is a polysaccharide.

37. A method according to claim 36, wherein said polysaccharide is selected from the group consisting of alginic acid, pectinic acid, hyaluronic acid, cellulose, chitosan, chitin, starch, dextran, heparin, chondroitin, cationic guar, cationic starch, carboxymethyl cellulose, carboxymethyl chitosan, carboxymethyl dextran, carboxymethyl starch, heparin sulfate, and chondroitin sulfate.

38. A method according to claim 36, wherein said polysaccharide is selected from the group consisting of alginic acid, pectinic acid, and hyaluronic acid, and their salts.

39. A method according to claim 34, wherein said polymer has been ionically crosslinked.

40. A method according to claim 39, wherein said solution further comprises a crosslinking agent selected from the group consisting of barium, calcium, strontium, and copper ions.

41. A method according to claim 39, wherein said polymer has been cationically crosslinked with an ionic crosslinking agent selected from the group consisting of barium, calcium, magnesium, strontium, boron, beryllium, aluminum, iron, copper, cobalt, lead, and silver ions.

42. A method according to claim 41, wherein said crosslinking agent is selected from the group consisting of barium, calcium, strontium, and copper ions.

43. A method according to claim 39, wherein said polymer has been cationically crosslinked with a crosslinking agent containing barium ions.

44. A method according to claim 39, wherein said elasticity agent contains one or more ions selected from the group consisting of sodium, potassium, magnesium, silver, ammonium, and lithium.

45. A method according to claim 39, wherein said solution is aqueous.

46. A method according to claim 45, wherein said amount of the elasticity agent is greater than about 0.5 percent by weight of the solution.

47. A method according to claim 45, wherein said amount of the elasticity agent is about 1–50 percent by weight of the solution.

48. A method according to claim 34, wherein said elasticity agent is nonionic and contains at least one hydroxyl or amine group.

49. A method according to claim 34, wherein said elasticity agent is selected from the group consisting of glucose, sorbitol, citric acid, urea, and glycerol.

50. A method according to claim 34, wherein said elasticity agent is sorbitol or urea.

51. A method according to claim 34, wherein said polymer is a polysaccharide and said elasticity agent is ionic.

52. A method according to claim 51, wherein said solution is aqueous.

53. A method according to claim 52, wherein said polysaccharide is alginic acid, pectinic acid, hyaluronic acid, cellulose, chitosan, chitin, starch, dextran, heparin, chondroitin, cationic guar, cationic starch, or a derivative or salt thereof.

54. A method according to claim 53, wherein said elasticity agent is selected from the group consisting of sodium, potassium, magnesium, silver, ammonium, and lithium ions, and mixtures thereof.

55. A method according to claim 34, wherein said polymer is a polysaccharide and the elasticity agent is nonionic.

56. A method according to claim 55, wherein said solution is aqueous.

57. A method according to claim 56, wherein said polysaccharide is alginic acid, pectinic acid, hyaluronic acid, cellulose, chitosan, chitin, starch, dextran, heparin, chondroitin, cationic guar, cationic starch, or a derivative or salt thereof.

58. A method according to claim 57, wherein said elasticity agent is selected from the group consisting of sorbitol, urea, and citric acid.

59. A method according to claim 34, wherein said polymer is alginic acid or a salt thereof crosslinked with barium or calcium ions, said solution is aqueous, and said elasticity agent is selected from the group consisting of potassium ions, sodium ions, sorbitol, glucose, citric acid, mannitol, dulcitol, and glycerol.

60. A method according to claim 59, wherein said elasticity agent is present in the solution in amount of from about 1 percent by weight to about 50 percent by weight.

61. A method according to claim 59, wherein the hydrogel composition further comprises a disintegrating agent selected from the group consisting of inorganic sulfates, inorganic phosphates, and magnesium ions.

62. A method according to claim 59, wherein the medical device is an elastically deformable stent having a retention feature, and in the exposing step the entire stent is exposed to the solution.

63. A method according to claim 34, wherein the hydrogel composition further comprises a disintegrating agent.

64. A method according to claim 63, wherein said disintegrating agent is selected from the group consisting of inorganic sulfates, ethylene diamine tetraacetic acid, ethylene diamine tetraacetate, citrates, organic phosphates, inorganic phosphates, phosphoric acid, trisodium carboxymethyloxy succinate, nitrilotriacetic acid, maleic acid, oxalate, polyacrylic acid, and sodium, potassium, calcium, and magnesium ions.

65. A method according to claim 34, wherein said polymer is a polysaccharide and the hydrogel composition further comprises an inorganic sulfate, inorganic phosphate, or magnesium ions.

66. A method according to claim 34, wherein the medical device is a stent, catheter, cannula, plug, or restrictor.

* * * * *

UNITED STATES PATENT AND TRADEMARK OFFICE
CERTIFICATE OF CORRECTION

PATENT NO. : 5,684,051
DATED : November 4, 1997
INVENTOR(S) : Samuel Anthony Thompson It is certified that error appears in the above-indentified patent and that said Letters Patent is hereby corrected as shown below:

Column 6, Line 2 - after "an" and before "mount" insert --a-- (to form amount).

Column 6, Line 4 - after "dissolving" and before "degrading" insert --,--.

Column 7, Line 64 - after "Calcium" delete "Aiginate" and insert --Alginate--.

Column 9, Line 39 - after "35" and before "of" insert --g--.

Claim 1, Column 11, Line 3 - after "an" and before "mount" insert --a-- (to form amount).

Signed and Sealed this

Fourteenth Day of April, 1998

Attest:

BRUCE LEHMAN

Attesting Officer            Commissioner of Patents and Trademarks